United States Patent [19]

Maraganore et al.

[11] Patent Number: 4,985,541

[45] Date of Patent: Jan. 15, 1991

[54] NOVEL CYTOTOXIC PROTEIN

[75] Inventors: John M. Maraganore, Waltham, Mass.; Wayne R. Kindsvogel, Seattle, Wash.

[73] Assignee: ZymoGenetics, Inc., Seattle, Wash.

[21] Appl. No.: 36,840

[22] Filed: Apr. 10, 1987

[51] Int. Cl.$^5$ .................. C07K 15/10; C07K 3/02; C07K 3/20; C07K 3/22

[52] U.S. Cl. ........................... 530/370; 530/350; 530/379; 530/396; 530/397; 530/412; 530/416; 530/417

[58] Field of Search ............. 530/370, 377, 396, 413, 530/416, 350, 379, 418, 422, 423; 514/21, 8

[56] References Cited

U.S. PATENT DOCUMENTS

| | | | |
|---|---|---|---|
| 3,060,165 | 10/1962 | Craig et al. | 530/370 |
| 4,340,535 | 7/1982 | Voisin et al. | 530/377 |
| 4,363,758 | 12/1982 | Masuho et al. | 530/370 |
| 4,450,154 | 5/1984 | Masuho et al. | 530/377 |
| 4,545,985 | 10/1985 | Pastan et al. | 424/85 |
| 4,689,401 | 3/1987 | Ferris | 530/377 |

FOREIGN PATENT DOCUMENTS

WO/85/03508  8/1985  PCT Int'l Appl. .................. 424/85

OTHER PUBLICATIONS

Chem Abstracts 105:202831u, Tsao et al., 1986.
C.A. 104:223320w, Yeung et al., 1986.
C.A. 95(4): 30276y, Wang, 1980.
C.A. 99: 68709n, Lee et al., 1983.
CA 99: 66554j; Wang et al., 1983.
CA 103: 189562u, Wong et al., 1985.
CA 97: 158247, Jin et al., 1982.
CA 98: 212361s, Zhang et al., 1982.
CA 85: 88802zb, Wang et al., 1976.
CA 95: 30276y, Shanghai Institute of Org Chem, 1980.
Shanghai Inst. of Organic Chem., *Nucleic Acids and Proteins*, The Proceedings of Symposium on Nucleic Acids and Proteins, Van Nostrand Reinhold Co., 1979, pp. 318-323.
Kezhan et al., *Scientia Sinica* 25:730-737, 1982.
Shanghai Institute of Experimental Biology, Second Laboratory, *Scientia Sinica* 19:811-827, 1976.
Cheng Kuo-Fen, *Obstet. Gynecol.*, 59:494-498, 1982.
Yeung et al., *Int. J. Peptide Protein Res.*, 27:325-333, 1986.
Stirpe et al., *J. Biol. Chem.*, 255:6947-6953, 1980.
Thorpe & Ross, *Immunological Rev.*, 62:119-158, 1982.
Vitetta and Uhr, *Cell* 41:653-654, 1985.
Kohler and Milstein, *Nature* 256:495-497, 1975.
Kohler and Milstein, *Eur. J. Immunol.*, 6:511-519, 1976.
Neuberger et al., *Nature* 312:604-608, 1984.
Casellas et al., *J. Biol. Chem.*, 259:9359-9364, 1984.
Heinrikson & Meredith, *Anal. Biochem.*, 136:65-74, 1984.
Ramakrishnan and Houston, *Science* 223:58-61, 1984.
Gasperi-Campani et al., *FEBBS Let.*, 76:173-176, 1977.
Gasperi-Campani et al., *Biochem. J.*, 186:439-441, 1980.
Olsnes, *Bull. Inst. Pasteur*, 74:85-99, 1976.
Lin et al., *Int. J. Peptide Protein Res.*, 12:311-317, 1978.
Irvin, *Arch. Biochem. Biophys.*, 169:522-528, 1975.
Seto et al., *Cancer Res.*, 42:5209-5215, 1982.
Vitetta and Uhr, *Ann. Rev. Immunol.*, 3:197-212, 1985.
Ross et al., *Eur. J. Biochem.*, 104:381-390, 1980.
Hwang et al., *Cell*, 48:129-136, 1987.
Bernhard et al., *Cancer Res.*, 43:4420-4428, 1983.

*Primary Examiner*—Margaret Moskowitz
*Assistant Examiner*—Jeff Kushan
*Attorney, Agent, or Firm*—Seed and Berry

[57] ABSTRACT

Purified cytotoxic proteins for use within therapeutic compositions are disclosed. The proteins inhibit protein synthesis in vitro, exhibit abortifacient activity in mice, and contain proline residues with equivalent positions at residue 43 and residue 46 in ricin A-chain. A method for preparing such a cytotoxic protein from the tissue of *Trichosanthes kirilowii* is also disclosed. The proteins may also be used within a method for inhibiting protein synthesis in selected cells.

6 Claims, 4 Drawing Sheets

```
        1                                    10
A:  Tyr Asp Val Ser Phe Arg Leu Ser Asp Ala Asn Ser Lys Ser 7           10                                   20
B:  Pro Ile Ile Asn Phe Thr Thr Ala Gly Ala Thr Val Gln Ser

20
A:  Tyr Arg Lys Phe Ile Thr Ser Leu Arg Asn Val Leu Pro Lys

30
B:  Tyr Thr Asn Phe Ile Arg Ala Val Arg Gly Arg Leu Thr Thr 30                                       39
A:  Ala Gly Glu Val Phe Asn (') Ile Pro (His) Leu Pro 40        43          46
B:  Gly Ala Asp Val Arg His Glu Ile Pro  Val Leu Pro
```

NOVEL CYTOTOXIC PROTEIN

TECHNICAL FIELD

The present invention relates to cytotoxic proteins in general, and more specifically, to the use of purified cytotoxic proteins within a variety of therapeutic compositions for treating selected cell types.

BACKGROUND ART

A variety of cytotoxic proteins have been derived from plant and bacterial sources. One such protein, trichosanthin, is an abortifacient protein extracted from the roots of *Trichosanthes kirilowii* (Shanghai Inst. Organic Chem., *Nucleic Acids and Proteins*, Proc. Symp. Nuc. Acids and Proteins, Van Nostrand Reinhold Co., 1979, 318-323). *T. kirilowii* is a plant which is indigenous to the Orient, and has been used in crude form in traditional Chinese medicine for centuries The protein is also known as Radix trichosanthes. It is a basic protein consisting of a single polypeptide chain of Mr 25,000 Da containing approximately 219 amino acid residues (Kezhan et al., *Scientia Sinica* 25: 730-737, 1982). The abortifacient activity of trichosanthin is apparently mediated through an effect on placental trophoblast cells (Shanghai Inst. Exp. Biol. Second Lab, *Scientia Sinica* 19: 811-827, 1976). Additional therapeutc applications of trichosanthn include treatment of ectopic pregnancy, benign and malignant hydatidiform mole and choriocarcinoma. Use of trichosanthin in treatment of choriocarcinoma is consistent with its abortifacient activity, as this uterine cancer is derived from fetal trophoblast cells. The abortifacient activity of trichosanthin is discussed by Cheng Kuo-Fen (*Obstet. Gynecol.* 59: 494-498, 1982). However, the mechanism of action of this protein has not been elucidated.

Yeung et al. (*Int. J. Peptide Protein Res.* 27: 325-333, 1986) purified three lectins from the roots of *Trichosanthes kirilowii*. These were shown to have erythroagglutinating activity, but not abortifacient activity.

As noted above, various cytotoxic proteins derived from plant and bacterial sources have also been described. Plant-derived toxins include abrin, isolated from *Abrus precatorious*, and ricin, isolated from *Ricinus communis*. Bacterial toxins include diptheria toxin and pseudomonas exotoxin. These molecules are structurally and functionally similar, being composed of a B-chain, which recognizes and binds to cell surface receptors, the B-chain being disulfide bonded to an A-chain which enters the cell and interferes with protein synthesis. A single molecule of such a toxin may be sufficient to kill a cell.

An additional class of cytotoxic proteins isolated from plants is exemplified by gelonin, an inhibitor of protein synthesis extracted from the seeds of *Gelonium multiflorum* (Stirpe et al., *J. Biol. Chem.* 255: 6947-6953, 1980). Unlike ricin and similar toxins, gelonin consists of a single polypeptide chain and does not exhibit generalized cytotoxic effects, apparently due to an inability to bind to and enter intact cells.

Recently, there has been considerable interest in producing therapeutic agents consisting of a cytotoxic protein coupled to a targeting agent such as an antibody (see review by Thorpe and Ross, *Immunological Rev.* 62: 119-158, 1982) or other protein such as a growth factor, which reacts with specific receptors on cells (Pastan et al., U.S. Pat. No. 4,545,985). Through the use of tumor-specific antibodies or other proteins that recognize markers which are highly expressed on the surface of tumor cells, these conjugates should exhibit specificity to tumor cells. However, these efforts have led to mixed results. Conjugates which comprise intact two-chain toxins may lack specificity due to their residual ability to bind nonspecifically to cells via the B-chain. Attempts to modify the toxin chemically to prevent nonspecific binding are not always successful and may reduce the activity of the A-chain. Conjugates using A-chain alone often have significantly lower potency as compared to whole toxin conjugates, apparently due to the role of the B-chain in mediating the entry of the toxin into the cell (Thorpe and Ross, ibid; Vitetta and Uhr, *Cell* 41: 653-654, 1985 and references therein). Furthermore, the use of ricin A-chain alone in an immunotoxin reduces generalized cytotoxicity by only one order of magnitude.

It is clear that many currently available immunoconjugates are unsuitable for cancer therapy due to a lack of specificity or lack of potency. Therefore, there is a need in the art for cytotoxic agents which by themselves lack generalized cytotoxicity, but which may be coupled to a targeting agent to produce a highly specific toxin conjugate. The present invention provides such a cytotoxic agent while further providing additional related advantages.

DISCLOSURE OF THE INVENTION

Briefly stated, the present invention discloses a purified cytotoxic protein suitable for use within cytotoxic compositions when covalently attached to a polypeptide capable of binding to the surface of mammalian cells. The cytotoxic protein or cytotoxic composition may be used within a therapeutic composition when combined with a physiologically acceptable carrier or diluent. The purified cytotoxic protein has the following properties: (a) it inhibits protein synthesis in vitro; (b) it exhibits abortifacient activity in mice; and (c) it contains proline residues with equivalent positions at residue 43 and residue 46 in ricin A-chain. The protein may be purified from root tissue of *Trichosanthes kirilowii*. In one aspect of the present invention, the protein has a molecular weight of approximately 25,000, as determined by polyacrylamide gel electrophoresis, and further, may contain the internal peptide sequence Ser-Val-Thr-Leu-Pro-Tyr-Ser-Gly-Asn-Tyr-Glu-Asn-Leu-Gln-Thr-Ala-Ala-Asp-Arg.

Figure 1:
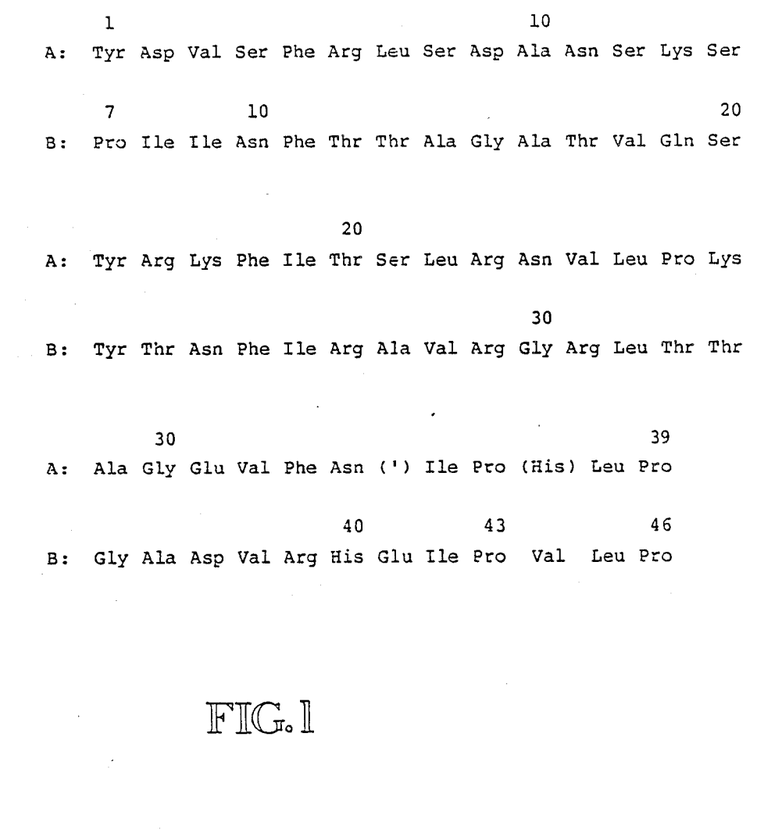
FIG. 1 depicts a comparison of the amino-terminal 39 residues of one form of trichosanthin-ZG (A) with the corresponding segment (residues 7–46) of the ricin A-chain (B). The sequences provided within this figure have been aligned to illustrate the homology between the two sequences. (') designates a gap which has been inserted in order to maximize homology. Amino acid residue numbers are indicated above the respective sequences.

In a related aspect of the present invention, the purified cytotoxic protein has the property of inhibiting protein synthesis in vitro, and comprises the amino acid sequence as shown in FIG. 1, beginning with tyrosine, number 1, and ending with proline, number 39.

In yet another aspect of the present invention, the purified cytotoxic protein has the following properties: (a) inhibits protein synthesis in vitro; (b) has a molecular weight, as determined by polyacrylamide gel electrophoresis, of approximately 25,000; and (c) contains the internal peptide sequence Ser-Val-Thr-Leu-Pro-Tyr-Ser-Gly-Asn-Tyr-Glu-Asn-Leu-Gln-Thr-Ala-Ala-Asp-Arg. Within a related aspect, the protein (a) inhibits protein synthesis in vitro; (b) consists of approximately 230 amino acid residues; (c) shares homology with the amino-terminal portion of ricin; and (d) contains the internal peptide sequence Ser-Val-Thr-Leu-Pro-Tyr-Ser-Gly-Asn-Tyr-Glu-Asn-Leu-Gln-Thr-Ala-Ala-Asp-Arg.

The present invention also discloses a method for preparing a cytotoxic protein from tissue of *Trichosanthes kirilowii.* The method generally comprises (a) treating a tissue sample from *Trichosanthes kirilowii* to obtain an aqueous extract; and (b) fractionating the extract by cation-exchange chromatography to obtain an enriched fraction. The method may also include, after the step of fractionating, fractionating the enriched fraction by high-performance liquid chromatography (HPLC) The initial step of fractionating may comprise chromatography on CM-Sephadex. It may also be advantageous to concentrate the enriched fraction prior to further fractionation.

As noted above, a variety of cytotoxic compositions utilizing the protein are also disclosed. The cytotoxic compositions generally comprise one of the proteins described above, covalently attached to a polypeptide capable of binding to the surface of mammalian cells. The polypeptide is most often an antibody or fragment thereof, and will generally be attached to the cytotoxic protein via disulfide bonds.

Yet another aspect of the present invention discloses therapeutic compositions which utilize the proteins described above. The therapeutic compositions generally comprise one such protein covalently attached to a polypeptide capable of binding to the surface of mammalian cells, and a physiologically acceptable carrier or diluent. Suitable carriers or diluents include sterile water, sterile saline, and liposomes.

A method of inhibiting protein synthesis in selected cells within a patient is also disclosed. The method generally comprises administering to the patient a therapeutic composition as described above, usually by intravenous injection or infusion.

Other aspects of the present invention will become evident upon reference to the following detailed description and attached drawings

BEST MODE FOR CARRYING OUT THE INVENTION

As noted above, the present invention describes the isolation and utilization of a trichosanthin-like protein (hereinafter "trichosanthin-ZG") from tissue of *Trichosanthes kirilowii,* preferably from root tissue of *Trichosanthes kirilowii.* This protein has been purified to homogeneity and is shown to be structurally distinguishable from the previously described trichosanthin (Shanghai Inst. Organic Chem., ibid.). Trichosanthin-ZG has been shown to be an effective abortifacient in mice, and has also been shown to inhibit protein synthesis in a rabbit reticulocyte lysate system. This protein shows homology in amino acid sequence with the catalytic A-chain of ricin (FIG. 1), particularly with regard to the presence of proline residues corresponding to proline residues at positions 43 and 46 in ricin A-chain. This homology is consistent with inhibitory effects of trichosanthin-ZG toward protein synthesis. However, unlike ricin, trichosanthin-ZG does not have a measurable toxic effect toward cell viability in the BeWo cell line (ATCC CCL98). In addition, in one aspect of the present invention the protein has an apparent molecular weight of ~25,000 Da, contains approximately 230 amino acid residues, and does not contain N-linked glycosidic linkages or cysteine residues. This lack of glycosylation is in sharp contrast to the structure of ricin A-chain and gelonin, which are glycoproteins.

In one aspect of the present invention, the protein contains an amino-terminal tyrosine residue. In a related aspect, the protein contains an amino-terminal aspartic acid. This variation is believed to be due to a processing event. It will be evident to one skilled in the art that other natural variations within the sequence could exist due to genetic polymorphisms.

In addition, substitutions for or deletions of the amino-terminal residue, as well as other nonessential amino acid residues, could be accomplished utilizing well-known recombinant techniques, without significantly affecting the inhibitory activity of the protein. It is believed, however, that the relative position of the proline residues may be important to the correct conformation of the protein.

Trichosanthin-ZG may be prepared from fresh or dry *T. kirilowii* roots (sometimes referred to as "root tubers"). The roots are treated to prepare an aqueous extract, preferably by grinding the tissue to a fine powder in a blender and dissolving the powder in a buffer at pH 5 to pH 8. A particularly preferred buffer is phosphate buffered saline (PBS, obtained from Sigma Chemical Co.). To ensure solubilization of the majority of the protein, the resulting solution is stirred overnight at 4° C. Insoluble material is then removed, preferably by filtration through a coarse filter, followed by centrifugation. The resulting extract is then fractionated by cation-exchange chromatography. Depending upon the buffer utilized for extraction, it may be necessary to remove excess salts prior to fractionation. Suitable chromatographic media include CM-Sephadex, SP-Sephadex and CM-Biogel A. Protein is eluted from the column with a pH 5 to pH 7 buffer containing about 0.3M to 0.6M NaCl. A particularly preferred buffer is 0.1M sodium phosphate pH 6.0, 0.3M NaCl. preferably, the protein-containing fraction is concentrated to facilitate further purification, such as by lyophilization followed by resuspension in a small volume of PBS. If desired, additional purification may be achieved by high-performance liquid chromatography using a reverse-phase column. The column matrix may contain acyl groups of varying length, preferably containing shorter groups such as tetrasilyl. The protein is eluted from the column using an increasing gradient of organic solvent. A preferred solvent system employs a gradient of 35% to 60% acetonitrile in 0.1% (w/v) trifluoroacetic acid (TFA) in water. The presence of trichosanthin-ZG may be monitored through purification by one or more of the following assays: (1) absorbance at 215 to 280 nm, (2) presence of a 25,000 Da band on polyacrylamide gel electrophoresis, and (3) activity assays as described herein.

As noted above, trichosanthin-ZG's lack of generalized cytotoxic effects on intact cells makes it a desirable component of a therapeutic cytotoxic agent. It is presumed that trichosanthin-ZG does not exhibit generalized cytotoxic effects due to a lack of receptors which recognize trichosanthin-ZG on most cell types. In contrast, ricin, abrin and diphtheria toxin are generally toxic to intact cells. Their use as components of immunoconjugates, therefore, carries certain risks, as they may uncouple from the targeting moiety. Trichosanthin-ZG therefore presents an attractive alternative to ricin and similar toxins.

The proteins described herein can be coupled to a targeting agent, such as an antibody, antibody fragment or other molecule (e.g., growth factor) which recognizes a specific cell surface marker, by conventional procedures. The targeting moiety of the resulting complex provides for cell binding and internalization. Extracellular release of trichosanthin-ZG from the complex will not result in general toxicity to the patient. This lack of generalized toxicity has been observed with immunoconjugates employing gelonin (Thorpe and Ross, ibid). Antibody-toxin complexes employing trichosanthin-ZG may be prepared by conventional procedures (see, for example, Greenfield et al., WO No. 85/03508, who disclose the use of spacer peptides to facilitate translocation and intracellular cleavage of toxin conjugates; Pastan et al., U.S. Pat. No. 4,545,985, who describe the conjugation of antibodies to toxins via a disulfide exchange reaction or via the formation of a thioether bond; and Thorpe and Ross (ibid.), who review methods for the preparation of antibody-toxin conjugates, including the use of chlorambucil derivatives, SPDP and haloacetyl derivatives). Typically, the antibody or other targeting moiety is covalently linked to the toxin through the use of a variety of bifunctional protein coupling agents, including chorambucil derivatives and agents which link the components via thiol groups.

Trichosanthin-ZG may be covalently bound to antibodies through the use of bifunctional reagents which first bind to primary amino groups (lysine residues) on the antibody and then form a second bond with the toxin molecule. A preferred cross-linking agent is N-succinimydl 3-(2-pyridyldithio) propionate (SPDP). SPDP is first reacted with free amino groups on the antibody through the succinimide ester portion of the cross-linking agent; the reaction is preferably performed at 20° C. in 0.05M borate buffer, pH 9.0, 0.3M NaCl. The derivatized antibody is then mixed, at neutral pH, with the toxin; and a disulfide exchange reaction ensues, resulting in the coupling of toxin and antibody via disulfide bonds. Alternatively, cystamine or 3, 3'-dimethyldithiobispropionate can be used to introduce free sulfhydryl groups onto the antibody, and the derivatized antibody is combined with the toxin as previously described. Conjugates can then be separated from both free toxin and uncoupled antibody by a combination of gel filtration (Jansen et al., Immunol. Rev. 62: 185, 1982; Neville and Youle, Immunol. Rev. 62: 75, 1982; Thorpe and Ross, ibid.) and affinity chromatography on Sepharose bound to the antigen of interest or to an anti-toxin antibody. The toxin conjugates can be assayed for antibody and toxin activities by radioimmunoassay and by killing of relevant target cells in vitro (see, for example, Vittetta et al., Immunol. Rev. 62: 159, 1982). Cell killing is typically monitored by measuring inhibition of protein synthesis using radioactive amino acids.

Preferably, immunoconjugates produced according to the present invention will utilize monoclonal antibodies. In general, monoclonal antibodies to particular cell surface antigens are prepared as described by Kohler and Milstein (Nature 256: 495–497, 1975 and Eur. J. Immunol. 6: 511–519, 1976). Briefly, spleen cells from mice immunized against the target antigen are fused to a myeloma-derived cell line, and hybrids are selected. The hybrid lines are then screened for production of the desired antibody, and cell lines of interest are selected and cloned. Secreted antibodies are then purified by conventional techniques. Suitable monoclonal antibodies may also be prepared by expressing cloned immunoglobulin genes in eukaryotic host cells. Methods for cloning and expressing immunoglobulin genes are well known in the art. See, for example, Boss et al. (published U.K. Patent Application No. 2,137,631), who describe the production of antibodies and antibody fragments in recombinant yeast; and Oi et al. (Proc. Natl. Acad. Sci. USA 80: 825–829, 1983), who transformed a lymphoid cell line with a rearranged kappa light-chain gene and observed the production of a novel recombinant antibody.

Alternatively, immunotoxins may be prepared by joining DNA sequences encoding antibodies or antibody fragments (e.g., Fab) to a genomic or cDNA fragment encoding trichosanthin-ZG and expressing the resultant hybrid sequence in a suitable host cell. Eukaryotic cells (including cultured mammalian cells and fungal cells) are preferred host cells in this regard. Methods for producing recombinant antibodies or antibody fragments in which a portion of the antibody has been replaced by a non-antibody polypeptide are described by Neuberger et al. (Nature 312: 604–608, 1984). Briefly, these researchers produced an enzymatically active Fab-nuclease hybrid protein which also bound antigen. The hybrid was expressed from a hybrid gene which had been transfected into J558L cells. DNA sequences trichosanthin-ZG may be prepared from Trichosanthes kirilowii tuber or other tissue by conventional molecular cloning procedures. It is generally preferable to use a cDNA so that no intervening sequences will be present. Techniques for preparing cDNA libraries are well known in the art (see, for example, Lawn et al., Cell 15: 1157–1174, 1978; and Michelson et al., Proc. Natl. Acad. Sci. USA 80: 472–476, 1983). Clones may be identified by using oligonucleotide probes, the sequences of which are determined from amino acid sequence data provided herein. It is preferred that such probes be at least 14 nucleotides in length in order to minimize false positive signals when screening DNA clones. Suitable probes may be synthesized by known methods (for review, see Itakura, in Trends in Biochemical Science, Elsevier Biochemical Press, 1982) or may be purchased from commercial suppliers. Alternatively, libraries may be probed using antibodies prepared against the purified protein to screen expression libraries (e.g., Young and Davis, Proc. Natl. Acad. Sci. USA 80: 1194–1198, 1983).

For in vivo therapeutic use, the immunoconjugates of the present invention may be mixed with a physiologically acceptable carrier or diluent. Such carriers or diluents will usually be inherently nontoxic and non-therapeutic. Suitable diluents in this regard include sterile water and sterile saline. Suitable carriers include liposomes. Therapeutic compositions may additionally contain stabilizers or preservatives. The immunoconjugates will typically be formulated at concentrations of about 1 mg/ml to 10 mg/ml. In addition, it may be beneficial to include compounds which potentiate the action of immunotoxins (see, for example, Casellas et al., *J. Biol. Chem.* 259: 9359-9364, 1984 and Ramakrishnan et al., *Science* 223: 58, 1984).

Typically, the immunotherapeutic compositions will be administered to patients intravenously, either by injection or infusion. Dose and treatment regimen will be determined according to the nature of the disease being treated and characteristics of the patient, including age, weight, physical conditions and disease history. Determination of treatment is well within the skill of those in the art. By way of example, the amount of immunotherapeutic composition administered will typically be in the range of about 0.1 to about 10 mg/kg of patient weight.

Additionally, immunoconjugates containing trichosanthin-ZG may be used in the treatment of bone marrow to remove metastatic tumor cells, where patients are undergoing autologous transplantation. In this application, it is preferred that the immunoconjugate be combined with a potentiating compound such as chloroquine (Ramakrishnan et al., ibid.), lysosomotropic amines or carboxylic ionophores (Casellas et al., ibid.).

Trichosanthin-ZG may also be useful as an abortifacient and in the treatment of ectopic pregnancy, hydatidiform mole and choriocarcinoma. Ectopic pregnancy will generally be treated by injection (intramuscular, intravenous or intraperitoneal) of purified trichosanthin-ZG in combination with a pharmaceutically acceptable carrier or diluent. Choriocarcinoma may be treated by administering a similar composition via intramuscular or intravenous injection. Hydatidiform mole may be treated via topical administration of trichosanthin-ZG in combination with a suitable carrier. In any event, it is preferable that patients be tested for an alergic reaction by use of a skin test (Kuo-Fen, ibid.) prior to treatment.

Trichosanthin-ZG may also exhibit an inhibitory effect upon mitogen-induced cell proliferation. The present invention may therefore also provide a useful therapeutic agent for control of metastasis in cancer.

To summarize the examples which follow, Example 1 describes a method for the purification of trichosanthin-ZG from dried root tissue of *T. kirilowii*. Example 2 discloses certain physical and chemical characteristics of trichosanthin-ZG. Example 3 describes the abortifacient and protein synthesis inhibitory activities of trichosanthin-ZG.

The following examples are offered by way of illustration and not by way of limitation.

EXAMPLES

EXAMPLE 1

Purification of Trichosanthin-ZG

Figure 2:
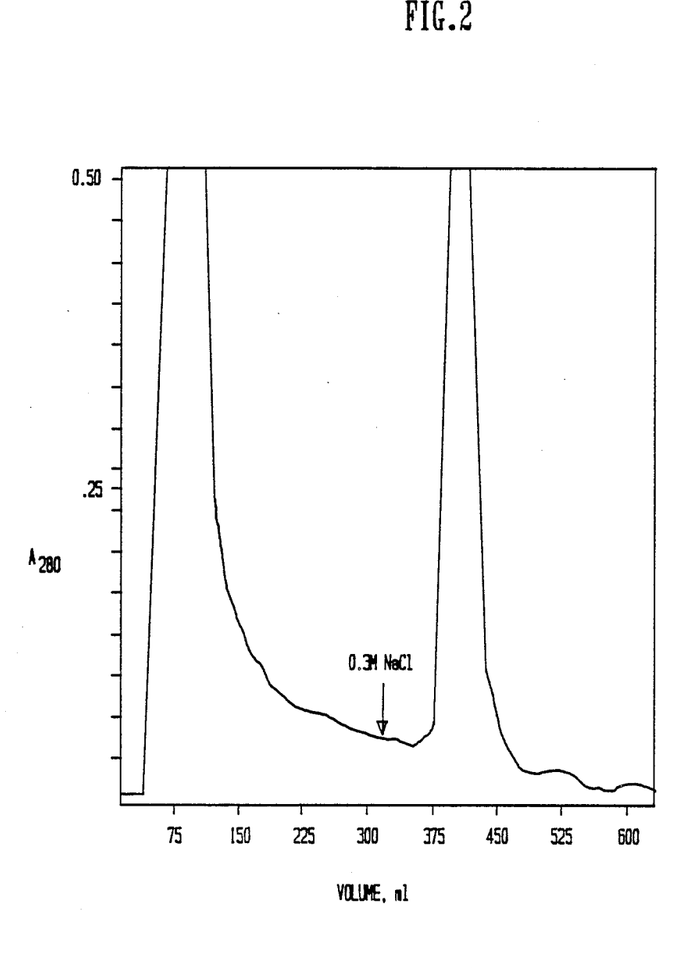
FIG. 2 depicts the fractionation of an aqueous extract of *Trichosanthes kirilowii* on CM-Sephadex.

Dried roots of *Trichosanthes kirilowii* were obtained from Hen Sen Herb Co., Seattle, Wash. Dried root tissue (27.25 g) from *T. kirilowii* was ground to a fine powder in a Waring blender and dissolved in 100 ml of a phosphate-buffered saline solution (PBS). The solution was filtered through cheesecloth to remove large, insoluble material and stirred overnight at 4° C. The homogenate was then dialyzed against 5 volumes of 0.1M sodium phosphate, pH 6.0. Following dialysis, the homogenate was centrifuged at $15,000 \times g$ for 15 minutes and thus clarified. The supernatant was applied to a column ($1.0 \times 50$ cm) of CM-Sephadex, equilibrated in 0.1M sodium phosphate, pH 6.0 (FIG. 2). A peak of $A_{280}$-absorbing material was eluted with a buffer containing 0.1M sodium phosphate, pH 6.0, and 0.3M NaCl. The effluent stream was monitored for absorbance at 280 nm and fractions were pooled and dialyzed extensively against PBS.

The flow-through and retained fractions were assayed for abortifacient activity as described below. Activity was found exclusively in the latter. The trichosanthin-ZG obtained from CM-Sephadex chromatography was maintained in PBS and stored at $-20°$. Examination of CM-Sephadex-purified trichosanthin on 15% SDS-PAGE revealed a single band at 25,000 Da. In further analyses, this material was found to be essentially free of other major protein contaminants. Approximately 3.9 mg of protein were obtained from 27.25 g of tuber.

Figure 3:
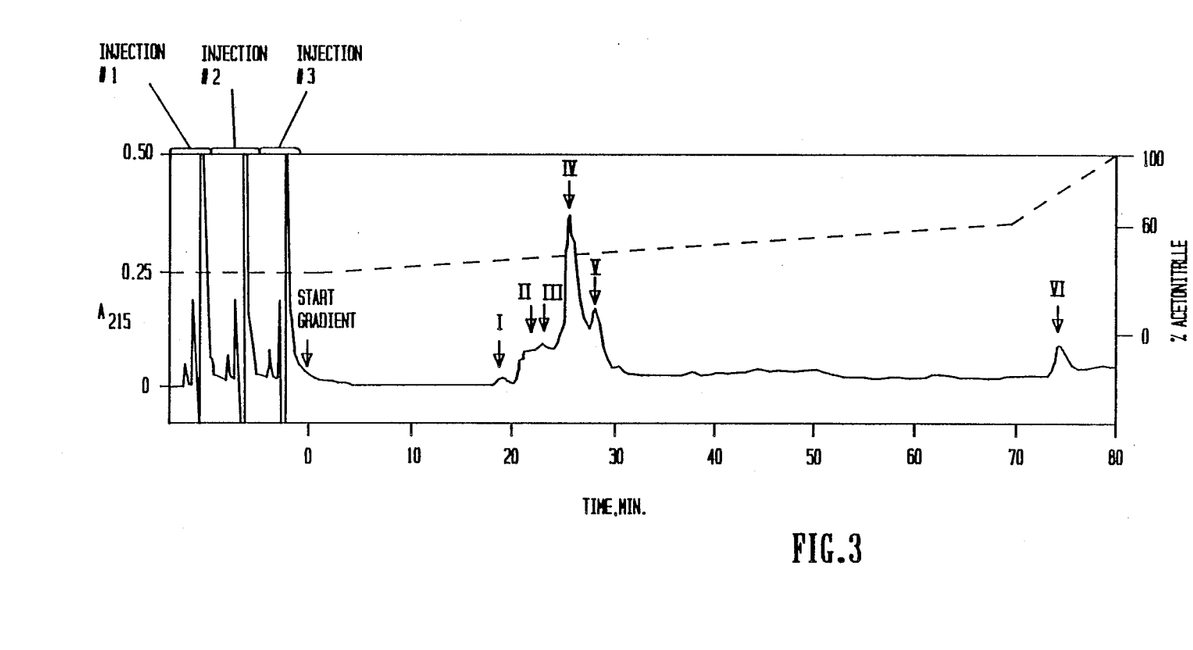
FIG. 3 depicts the fractionation of the major protein-containing faction from CM-Sephadex chromatography on a reverse-phase HPLC column. Pool IV contained the protein of interest. Details of the purification procedure are given in Example 1.
Figure 4:
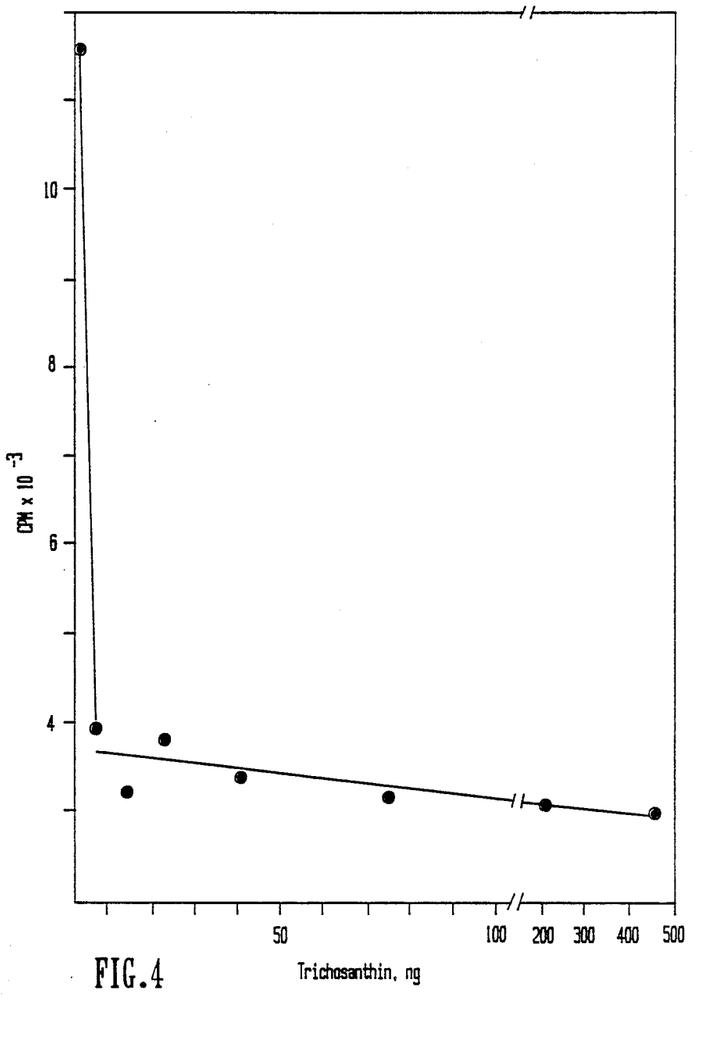
FIG. 4 illustrates the effect of trichosanthin-ZG on protein synthesis in a reticulocyte lysate system.

Final purification of trichosanthin-ZG was achieved by reverse-phase, high-performance liquid chromatography (HPLC), employing a Varian LC 5000 chromatographic system and a Vydac $C_4$ column ($0.46 \times 25$ cm) (FIG. 3). Three injections of 1 ml of a solution containing trichosanthin-ZG in PBS (at a concentration of 70 ug/ml) were applied to the Vydac $C_4$ column equilibrated in a water/acetonitrile solvent system which contained 0.1% trifluoroacetic acid (flow rate—1.5 ml/min). Initial chromatographic conditions were established at 35% acetonitrile in the 0.1% TFA solvent, and the column was developed with a linear gradient of increasing acetonitrile concentration (from 35% to 60%) over 60 minutes. The effluent stream was monitored for absorbance at 215 nm and fractions of 1.5 ml were collected. Based upon the elution of $A_{215}$-absorbing material, six pools were made and labeled I-VI (FIG. 3). Pools I-VI were lyophilized. The dried pools were redissolved in a known volume of 5% acetic acid, and aliquots were by 15% SDS-PAGE under reducing and non-reducing conditions. A single band of 25 KDa (in the presence and absence of reductant) was identified in a lane containing material from pool IV. No other proteinaceous material was detected in pools I-III, V and VI, as visualized by coomassie staining. This peak was subsequently shown to consist of two isozymes by automated Edman degradation.

EXAMPLE 2

Characterization of Physical and Chemical Structure of Trichosanthin-ZG

Amino acid analysis of HPLC-purified trichosanthin-ZG was performed by hydrolysis of protein in 6N HCl vapor, in vacuo, at 110° C. for 24 hours. Amino acids were derivatized prior to separation with phenylisothiocyanate (PITC) essentially as described by Heinrikson and Meredith (*Anal. Biochem.* 136: 65-74, 1984) and phenylthiocarbamylamino acids (PTC-amino acids) were separated by reversephase HPLC. PTC-amino acid analysis was performed using a Varian LC-5500 chromatography system, a Varan Vsta 400 Data Analyzer, and an IBM octadecylsilyl column ($0.46 \times 25$ cm). Reduced and S-carboxymethylated trichosanthin-ZG was subjected to PTC-amino acid analysis in order to determine the presence of cysteine. The phenylthiocarbamyl derivative of S-carboxymethyl cysteine has been shown to elute between PTC-Glu and PTC-Ser in the chromatographic system used.

Amino acid analysis of intact trichosanthin-ZG (Table 1) reveals a composition marked by a high content of serine (7.7%). Also notable in the composition of the protein is a single mole of histidine per mole of protein. Amino acid analysis of the reduced and S-carboxymethylated polypeptide displays an absence of cysteine. The amino acid composition of this protein differs significantly from that of trichosanthin isolated by Shanghai Inst. Exp. Biol. Second Lab, ibid.

TABLE I

| Amino Acid | Moles Amino Acid/Mole Protein | Amino Acid | Moles Amino Acid/Mole Protein |
|---|---|---|---|
| Asx | 20 | Tyr | 12 |
| Glx | 19 | Val | 18 |
| Ser | 18 | Met | 5 |
| Gly | 9 | Ile | 16 |
| His | 1 | Leu | 26 |
| Arg | 15 | Phe | 13 |
| Thr | 15 | Lys | 11 |
| Ala | 26 | Trp | N.D. |
| Pro | 10 | Cys | 0 |

As a measurement of potential glycosidic linkages in trichosanthn-ZG, the protein was applied to 15% SDS-PAGE and stained with PAS stain (Fairbanks et al., *Biochemistry* 10: 2026–2031, 1971). Alternatively, trichosanthin-ZG was treated with N-glycanase (Hirani and Rasmussen, *Hoppe-Seylers Z. Physiol. Chem.* 367: 191–195, 1986) (Genzyme Corporation, Boston, Mass.) and applied to 15% SDS-PAGE. No alteration in electrophoretic mobility on SDS gels was noted.

Automated Edman degradation was performed on intact trichosanthin-ZG and this analysis allowed for determination of the N-terminal 38 residues of the protein. Sequence analysis of the intact protein was performed using an Applied Biosystems 470A gas-phase sequenator. Phenylthiohydantoins were analyzed using an Applied Biosystems 120A PTH-analyzer. Sequence analysis identified a heterogeneity at the N-terminus of the protein. In particular, trichosanthin-ZG as purified is a mixture of two polypeptide chains: one contains a tyrosine at its N-terminus, the other does not. We have labeled these two forms of the protein at (Tyr-1) and (Asp-1) trichosanthin-ZG, respectively. The (Tyr-1) derivative represents ~70% of the mixture. Results from sequence analyses as they apply to the predominant (Tyr-1) form of the protein are shown in FIG. 1. As shown in FIG. 1, the amino terminal sequence of trichosanthin-ZG is homologous to that of ricin A-chain.

EXAMPLE 3

Biological Activities of Trichosanthin-ZG

Trichosanthin-ZG was tested for abortifacient activity in mice. Pregnant mice were injected intravenously on day 12 with two separate doses of 7.8 μg of CM-Sephadex-purified protein in PBS (100 μl) administered at a 12-hour interval. On day 13, the mice were autopsied and the number of fetuses and their viability was determined by inspection. Results shown in Table II indicate that the protein is an effective abortifacient.

TABLE II

| Mouse # | # Fetuses | # Fetuses Dead | % Abortion |
|---|---|---|---|
| 1 | 10 | 10 | 100 |
| 2 | 12 | 12 | 100 |
| 3 | 20 | 20 | 100 |
| 4 | 3 | 3 | 100 |
| 5 | 3 | 3 | 100 |

The ability of trichosanthin-ZG to inhibit protein synthesis in a cell-free translation system was analyzed using a reticulocyte lysate system kit and L-[$^3$H]-leucine, both from New England Nuclear, Boston, Mass.; this system employs a modification of the method of Pelham and Jackson (*Eur. J. Biochem.* 67: 247–256, 1976). Messenger RNA used was supplied by the manufacturer. Lysates were incubated at 37° C. for 1 hour and frozen prior to analysis. The level of protein synthesis was measured by spotting aliquots of the lysate on test TLC strips supplied by the manufacturer. The strips were developed in a solvent of methanol: water: trichloroacetic acid: glacial acetic acid (30:50:10:10, v/v/w/v). The strips were cut in half to separate developed and non-developed (i.e., that at the origin) material and [$^3$H] radioactivity was measured in the latter. The incorporation of radioactivity in TCA-precipitable material was found to be linear to concentration of mRNA. The amount of trichosanthin-ZG used in this assay system varied from 7 ng to 450 ng. Results (FIG. 4) indicate that less than 10 ng of the purified protein is sufficient to stop cell-free translation in the assay system. Additional experiments indicated that the inhibition of protein synthesis was not due to a ribonuclease activity.

We claim:

1. A purified cytotoxic protein having the following properties:
   inhibits protein synthesis in vitro;
   exhibits abortifacient activity in mice;
   does not contain N-linked glycosidic linkages;
   has an amino acid composition consisting essentially of, in moles of amino acid per mole of protein,

| | | | |
|---|---|---|---|
| Asx | 20 | Pro | 10 |
| Glx | 19 | Tvr | 12 |
| Ser | 18 | Val | 18 |
| Gly | 9 | Met | 5 |
| His | 1 | Ile | 16 |
| Arg | 15 | Leu | 26 |
| Thr | 15 | Phe | 13 |
| Ala | 26 | Lys | 11; | has a molecular weight as determined by polyacrylate gel electrophoresis of approximately 25,000 Daltons; and
   contains the amino-terminal amino acid sequence: X-Asp-Val-Ser-Phe-Arg-Leu-Ser-Asp-Ala-Asn-Ser-Lys-Ser-Tyr-Arg-Lys-Phe-Ile-Thr-Ser-Leu-Arg-Asn-Val-Leu-Pro-Lys-Ala-Gly-Glu-Val-Phe-Asn-Ile-Pro
   wherein X is tyrosine or H.

2. The protein of claim 1 wherein said protein is purified from root tissue of *Trichosanthes kirilowii.*

3. A method for preparing a cytotoxic protein from tissue of *Trichosanthes kirilowii* comprising:
   treating a tissue sample from *Trichosanthes kirilowii* with an aqueous buffer to obtain an aqueous solution containing a protein according to claim 1; and
   fractionating the solution by cation exchange chromatography to obtain a fraction enriched for said protein.

4. The method of claim 3, including, after the step of fractionating, fractionating the enriched fraction by high-performance liquid chromatography.

5. The method of claim 3 wherein said tissue is root tissue.

6. The method of claim 3 wherein the step of fractionating comprises chromatography on CM-Sephadex.

* * * * *

UNITED STATES PATENT AND TRADEMARK OFFICE
CERTIFICATE OF CORRECTION

PATENT NO.   :   4,985,541
DATED        :   January 15, 1991
INVENTOR(S)  :   John M. Maraganore et al.

It is certified that error appears in the above-identified patent and that said Letters Patent is hereby corrected as shown below:

In column 3, line 52, please delete "faction" and substitute therefor --fraction--.

In column 4, line 50, please delete "25".

In column 6, line 42, after "sequences" please insert --encoding--.

In column 10, claim 1, line 2 of the graph, please delete "Tvr" and substitute therefor --Tyr--.

In column 10, claim 1, lines 44 and 45, please delete "polyacrylate" and substitute therefor --polyacrylamide--.

Signed and Sealed this

Eighteenth Day of August, 1992

*Attest:*

DOUGLAS B. COMER

*Attesting Officer*     Acting Commissioner of Patents and Trademarks